United States Patent
Ustuner

(10) Patent No.: US 6,746,402 B2
(45) Date of Patent: Jun. 8, 2004

(54) ULTRASOUND SYSTEM AND METHOD

(75) Inventor: E. Tuncay Ustuner, 405 Stierlin Rd., Apt. 16, Mountain View, CA (US) 94043

(73) Assignee: E. Tuncay Ustuner, Mountain View, CA (US)

( * ) Notice: Subject to any disclaimer, the term of this patent is extended or adjusted under 35 U.S.C. 154(b) by 0 days.

(21) Appl. No.: 10/324,690

(22) Filed: Dec. 19, 2002

(65) Prior Publication Data

US 2003/0125629 A1 Jul. 3, 2003

Related U.S. Application Data

(60) Provisional application No. 60/345,801, filed on Jan. 2, 2002, and provisional application No. 60/356,036, filed on Feb. 11, 2002.

(51) Int. Cl.[7] ................................................ A61B 5/02
(52) U.S. Cl. ................................................... 600/462
(58) Field of Search ........................... 600/437, 443, 600/447, 459; 128/898

(56) References Cited

U.S. PATENT DOCUMENTS

| | | | |
|---|---|---|---|
| 4,086,916 A | 5/1978 | Freeman et al. | |
| 4,545,386 A | 10/1985 | Hetz et al. | |
| 4,744,368 A | 5/1988 | Young et al. | |
| 4,869,260 A | 9/1989 | Young et al. | |
| 4,898,177 A | 2/1990 | Takano et al. | |
| 4,972,889 A | * 11/1990 | Angelsen | 600/463 |
| 5,088,500 A | 2/1992 | Wedel et al. | |
| 5,152,293 A | 10/1992 | Vonesh et al. | |
| 5,195,519 A | 3/1993 | Angelson | |
| 5,261,404 A | * 11/1993 | Mick et al. | 600/407 |
| 5,284,147 A | 2/1994 | Hanaoka et al. | |
| 5,482,047 A | 1/1996 | Nordgren et al. | |
| 5,598,846 A | 2/1997 | Peszynski | |
| 5,640,960 A | 6/1997 | Jones et al. | |
| 5,671,747 A | 9/1997 | Connor | |
| 5,709,219 A | * 1/1998 | Chen et al. | 600/587 |
| 5,752,517 A | 5/1998 | Harman et al. | |
| 5,765,565 A | * 6/1998 | Adair | 128/849 |
| 5,792,059 A | 8/1998 | Furia et al. | |
| 6,023,372 A | 2/2000 | Spitzer et al. | |
| 6,029,530 A | 2/2000 | Patton et al. | |
| 6,106,472 A | 8/2000 | Chiang et al. | |
| 6,126,608 A | * 10/2000 | Kemme et al. | 600/459 |
| 6,142,946 A | 11/2000 | Hwang et al. | |
| 6,248,072 B1 | 6/2001 | Murkin | |
| 6,319,201 B1 | * 11/2001 | Wilk | 600/437 |
| 6,416,475 B1 | 7/2002 | Hwang et al. | |
| 6,500,119 B1 | * 12/2002 | West et al. | 600/437 |
| 6,530,887 B1 | * 3/2003 | Gilbert et al. | 600/459 |
| 2001/0031924 A1 | 10/2001 | Seward | |
| 2002/0016545 A1 | 2/2002 | Quistgaard et al. | |
| 2002/0045805 A1 | 4/2002 | Gopinathan et al. | |
| 2002/0075232 A1 | 6/2002 | Daum et al. | |

* cited by examiner

*Primary Examiner*—Francis J. Jaworski
(74) *Attorney, Agent, or Firm*—Toler, Larson & Abel L.L.P.

(57) ABSTRACT

A surgery dedicated ultrasound system is described. The system is used for imaging and/or guidance and/or controlling purposes. The surgeon uses and controls the system and accesses the information obtained and processed through the system while performing surgery.

50 Claims, 15 Drawing Sheets

ULTRASOUND SYSTEM AND METHOD

CROSS REFERENCE TO RELATED APPLICATIONS

The present application claims priority from U.S. Provisional Patent Application No. 60/345,801, filed Jan. 2, 2002, entitled "An Ultrasound System and Method of Performing Surgery" by Tuncay Üstüner, and claims priority from U.S. Provisional Application No. 60/356,036, filed Feb. 11, 2002, entitled "Intraoperative Doppler Ultrasound System and a Method of Performing Surgery" by Tuncay Üstüner the contents of which are incorporated herein.

FIELD OF THE INVENTION

The present invention relates to medical ultrasound systems and methods.

BACKGROUND

In conventional medical ultrasound devices, transducers mounted in a hand-held probe work both as a source of an ultrasound pulse and as a receiver of the echo. The received echoes are converted to electric signals which are then processed into visual and/or audio information.

Recent technological advances have improved the B-Mode image quality significantly. Colored images of blood flow are now routine clinical tools. Systems that provide static 3-D images and even real-time 3-D images have also entered the market.

Despite these advances, a surgery dedicated ultrasound system that does not interrupt or interfere with the surgical process but enables surgeons to detect and obtain information about anatomical and pathological surfaces and structures just before or during dissecting has not been provided. It would be particularly desirable if surgeons were capable of reorienting themselves easily and to reassess tissue types, borders, etc. during surgery. Also, it would be desirable to use medical ultrasound systems as a medical tool to perform faster and safer surgeries.

Accordingly, there is a need for an improved ultrasound system specifically designed for surgeon use during a surgery.

SUMMARY

The present invention is directed to an ultrasound system especially suited for use during surgery. In one embodiment, the ultrasound system includes a wearable ultrasonic probe in combination with a display positioned within the sterile operating field and coupled via a processor to the probe. In a particular embodiment the probe, display and the processor of a completely wearable ultrasound system are worn on the hand of a surgeon. In other embodiments, the display is worn by the surgeon but is not positioned within the sterile operating field, or the display is carried by an articulated arm and is positioned near the surgical site. Also methods for using an ultrasound system during a surgery are disclosed. One embodiment includes placing a wearable ultrasonic probe of an ultrasound system onto a hand of a surgeon and using the ultrasound system during the surgery to provide display information to the surgeon while the surgeon's head is positioned to view the surgical site.

DETAILED DESCRIPTION

Figure 1:
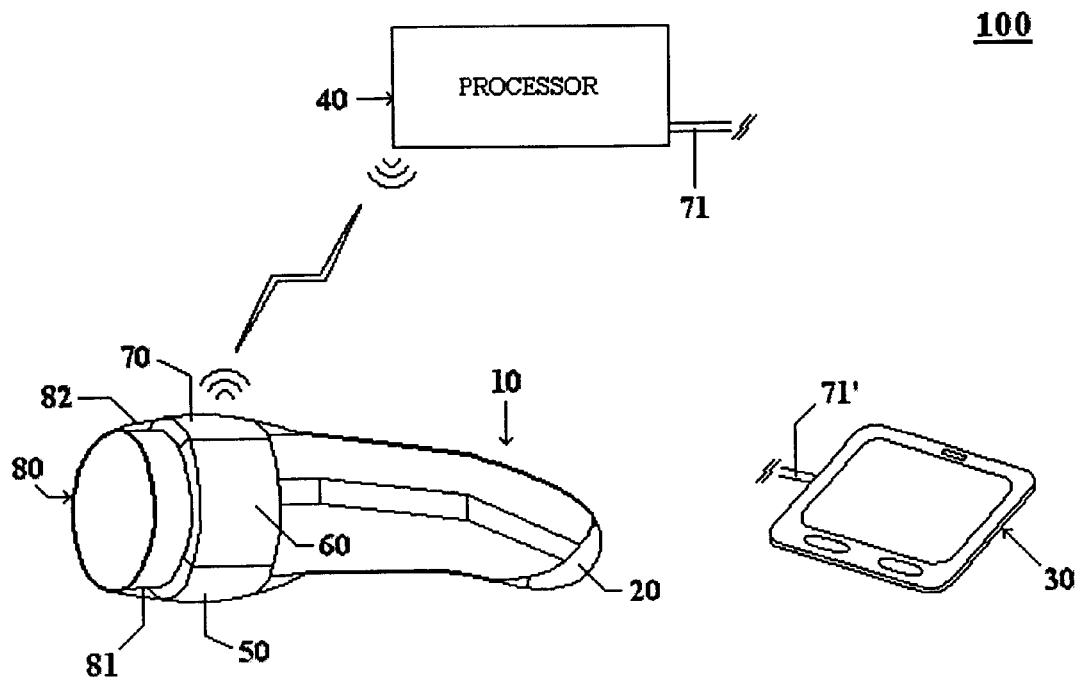
FIG. 1 is a general diagram that illustrates a particular embodiment of an ultrasound system.

Basic elements of an ultrasound system 100 are shown in FIG. 1, including a probe 10, a processor 40, and a display 30. Some embodiments may have peripheral elements such as one or more tape recorders, video cassette recorders, DVD players and/or recorders, cameras, printers, computers, etc.

The illustrated probe 10 accommodates at least one ultrasound transducer 20 and is wearable on a surgeon's hand, preferably on at least one of the third, fourth or fifth fingers, for example like a glove finger or a thimble. The system may use more than one probe, each worn on a different finger at the same time.

The transducer 20 is placed preferably at the tip of the finger. More than one transducer can be placed around the distal end of the finger.

The transducer 20 can be one of various different kinds, such as a piezoelectric ceramic transducer, a piezoelectric polymer transducer, a piezoelectric ceramic/polymer composite transducer or a micromachined ultrasonic transducer, for example. The term "transducer" is intended broadly, and should not be limited to any specific type of ultrasonic transducer or transducer material.

The transducer 20 can be comprised of a single element or multiple elements. When multiple elements are used, they can each face in the same or in different line of sight. The transducer 20 can be a 1D, 1.25D, 1.5D, 1.75D or 2D array transducer. The transducer 20 can also be an array of elements able to electronically steer to a multitude of lines of sight and/or focus to a multitude of depths. The transducer 20 can be fixed in position or mechanically scanned along a multitude of lines of sight. Alternatively, the beam from a fixed position transducer can be scanned by a rotating/wobbling mechanical mirror to a range of directions. The transducer 20 can also be a single element transducer with a mechanical lens in front of it focusing the beam at a fixed depth. In another embodiment, the transducer 20 can have multiple elements arranged as annular rings which are able to focus at a multitude of depths. If the annular array has a fixed mechanical focus, the diameter of the active aperture can be variable as a function of depth.

The transducer 20 emits an ultrasonic pulse generated by a transmitter at a controllable pulse repetition rate. This pulse is preferably a wide bandwidth pulse, though this is not a requirement of this invention. The echo from tissue after each firing is received by the transducer 20 and processed by a receiver. The receiver functions can include pre-amplification, time gain compensation to compensate for tissue attenuation and, in the case of an array transducer, beam formation. The receiver output is an echo signal from a certain direction (line of sight) as a function of time. It can be a radio frequency (RF) signal, intermediate frequency (IF) signal or a baseband signal. The output of the receiver is fed to the processor 40 to undergo further signal processing.

The display 30 of the system presents visual and/or audio and/or tactile information to the surgeon or other person. As used herein, the term "display" is intended broadly to refer to a device for presenting display information in any one or more of the visual, audio and tactile modes, unless the context clearly indicates that the intended meaning is more limited. The system may have more than one display. If there are assisting persons to the surgeon, who need the same information obtained through the system, they may be provided with their own personal displays.

The display 30, when configured to convey visual information, can be as simple as one or more Light Emitting Diodes (LEDs). In the embodiments where the visual output is an image, the display is preferably a flexible, flat-panel display such as an LCD. Alternatively, the display can project visual information onto a surface positioned close to the surgeon's line of sight. This surface can be a screen positioned in the sterile operating field near the surgical site or incision, a surface of a surgical drape near the surgical site or incision, or even a surgeon's retina. The visual information presented by the display can include two or three dimensional, B-mode, Color Doppler, or mixed-mode images. When 3-D images are displayed, the 3-D volume can be constructed by scanning a transducer array electronically or mechanically in two dimensions. If the transducer does not have electronic or mechanical scanning means, the surgeon can perform the scanning by moving the probe around the region of interest. The 3-D volume image can be assembled from multiple lines of sight data by using a probe position and direction sensor.

The wearable forms of the visual display include a head mounted display, such as a display in the form of eyewear or a display attached to eyewear. Then the visual display information from the surgical ultrasound system is superimposed on the surgeon's visual field. Other alternative wearable forms of the visual displays are worn on the hand, wrist, or forearm of the surgeon's hand that wears the probe, or on the surgeon's other hand, wrist or forearm.

When the display is configured for audio output, it can include an earphone or a speaker. The speakers can be positioned anywhere in the operating room, on the probe, processor, or on a visual display. The parameters of interest can be used to modulate the amplitude or frequency of the audio display information. Directional information can be provided through a stereo output. Alternatively, a synthesized human voice can be used to provide at least some of the audio display information in spoken language.

When the display is configured for tactile output, it is generally wearable. It is worn either as part of the probe or on any part of the body. It preferably uses touch stimuli to convey tactile display information derived through the system.

In some embodiments, the processor 40 is also wearable. The processor may be worn together with the probe 10 and/or the display 30, or worn separately. In some embodiments the processor 40 is integrated with the display 30 and is worn or positioned together with the display 30 as a unit, but the probe 10 is separately worn. In other embodiments the processor 40 is worn together with the probe 10, and the display 30 is worn or positioned separately. Yet in some other embodiments the probe 10, display 30 and the processor 40 are integrated and they are worn all together.

The processor 40 in this non-limiting example is an element that includes the processing circuitry other than the parts of the processing circuitry that may be contained inside the probe 10 or inside the display 30 of the ultrasound system in different embodiments. The processing circuitry will often encompass a front-end processor which may include an A/D converter, a beamformer, front-end filters, etc., and a back-end processor which may include multiple subprocessors such as a mid-processor (Spectral Doppler processing, Color Flow processing, filtering etc.), a frame processor (scan converter, image memory etc.), a video processor (amplitude detector, video filters, etc), an audio processor, etc., depending on the embodiment. The processor includes analog and/or digital signal processors and may be programmable and/or non-programmable. The term "processor" is intended broadly and should not be limited to any specific type or capacity of signal processing system.

The ultrasound system, for example as shown in FIG. 1, may also have a user interface 50 on one or more of its constituent elements or units. Preferably at least one user interface is included on a wearable element or unit. When a user interface is placed on the probe 10, it is preferably placed on the volar surface of the proximal or middle phalanx. The user interface 50 can include means to turn the system on or off.

In a particular embodiment, the system is turned on to a stand-by state with the user interface 50. A contact sensor is positioned at the tip of the probe. When the contact sensor senses contact with an adjacent surface (such as a tissue surface at a surgical incision of a surgical site), the contact sensor sends a trigger signal to activate the system waiting at the stand by state. The system can be turned on or off directly by the contact sensor. In this embodiment the contact sensor may be the only user interface.

Preferably the user interface 50 also includes means to adjust the sensitivity of the system and to show the status of the system. The user interface may also have means to switch among different operating modes such as audio, visual, both audio and visual, B-Mode, arteries-only, etc. The system can also include a user interface that is voice activated.

Any element or unit of the ultrasound system can be powered by a battery, such as battery 60 illustrated in FIG. 1. Use of a battery provides for increased mobility and wearability by the surgeon.

In the embodiments where certain system elements are separate from each other, any two or more of the constituent elements or units of the system can communicate through cables 71, or through a wireless link 70 that may include, for example, infrared, radio frequency, laser, microwave, or ultrasound transmitter/receivers. Where the probe communicates wirelessly the echo signals are preferably at least partially beamformed in the probe before being transmitted to the processor, thereby reducing the required transmission bandwidth.

The wearable elements or units of the system are lightweight and low profile. They conform to the dynamic contours of the anatomy that they correspond to when they are worn. The wearable parts that cross the joints are flexible to avoid limits on joint movements.

In a particular embodiment, the elements of the system that are worn on the hand are placed in pockets between an inner layer 81 and outer layer 82 of a cover 80 made of a material which has elastic properties like rubber for snug fit and flexibility. Where required, this cover is strengthened with a harder material like plastic. The inside surface of the inner layer of the cover that contacts the surgeon's finger or the surgical glove can be made to prevent slippage. At least the portion of the outer layer that covers the ultrasound transducer is preferably acoustically transparent, and the whole outer surface is preferably made of a smooth material.

Figure 2:
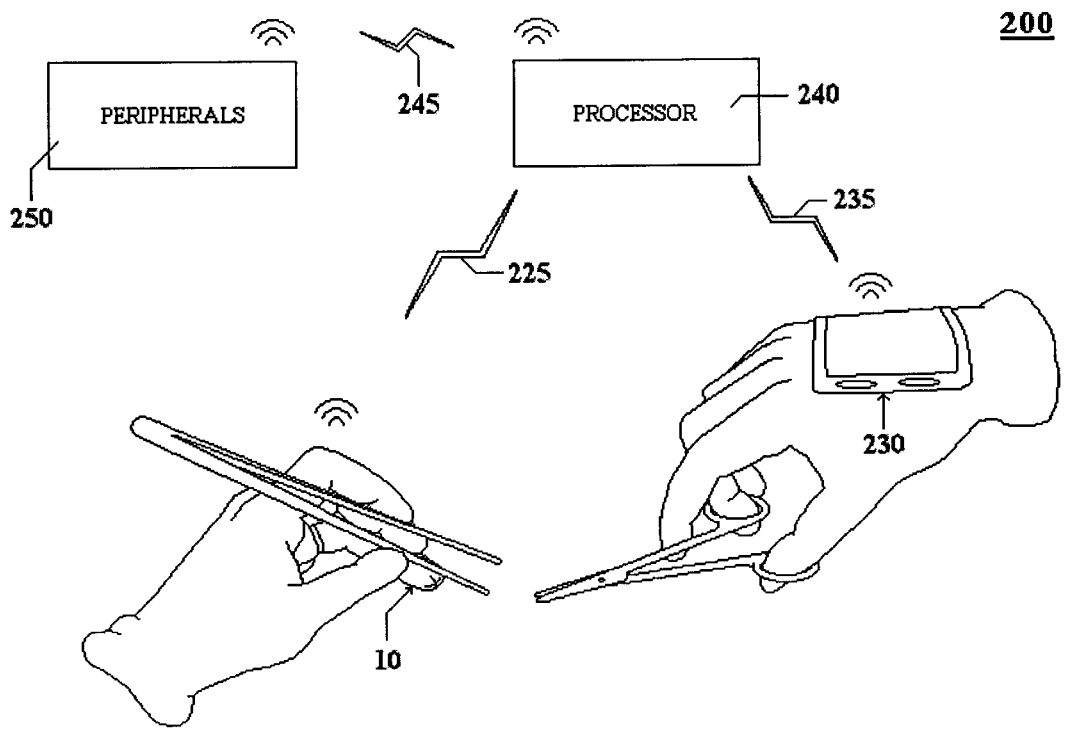
FIG. 2 is an illustrative embodiment of an ultrasound system.

Referring to FIG. 2, an ultrasound system 200 is illustrated. The ultrasound system 200 includes the fingertip probe 10 of FIG. 1, a wearable display 230, and a separate processor 240. The display 230 includes a lightweight visual display panel configured to be worn on the back of one of the surgeon's hands. The processor 240 communicates wirelessly via a first wireless link 225 with the probe 10. The processor 240 also communicates wirelessly with the display 230 via a second wireless link 235. In addition, the processor 240 may communicate with remote peripherals 250 via a wireless interface 245. The processor 240, display 230, and probe 10 each include the necessary wireless transceiver hardware and other logic control to implement the wireless communication capability.

Figure 3:
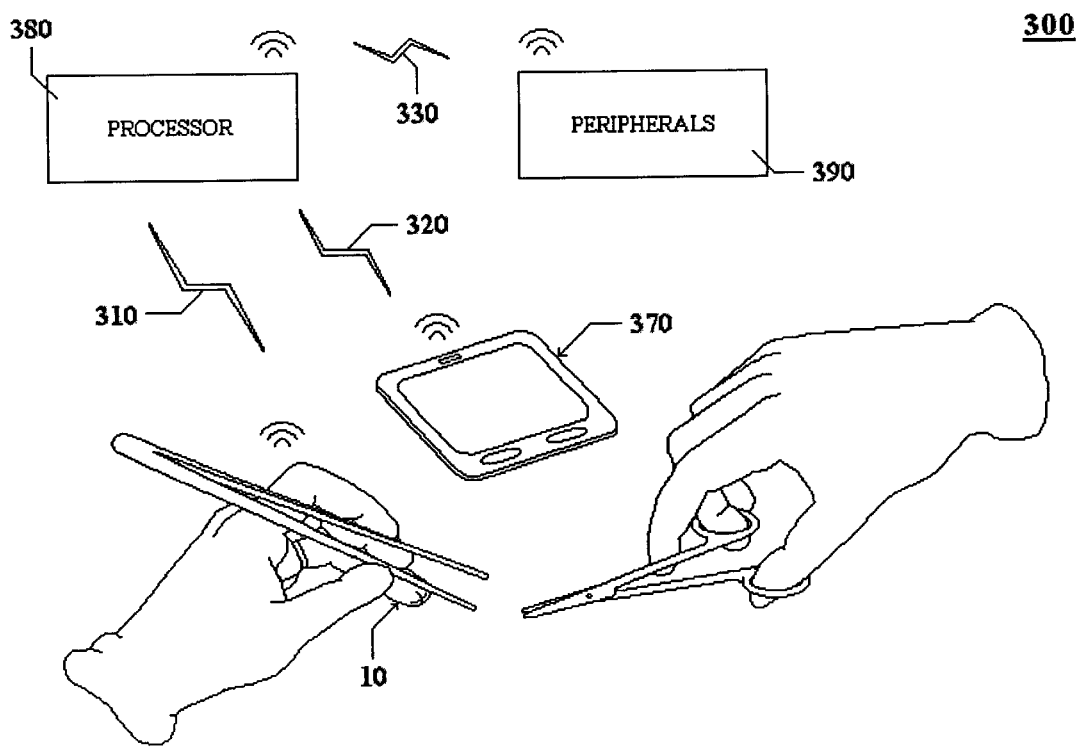
FIG. 3 is a general diagram that illustrates another embodiment of the ultrasound system.

Referring to FIG. 3, another embodiment of an ultrasound system 300 is illustrated. In this embodiment, the ultrasound system 300 includes the probe 10 of FIG. 1, a movable display 370, a processor 380, and remote optional peripherals 390. The processor 380 communicates with the probe 10 and the movable display 370 via wireless links 310 and 320. The processor 380 also communicates with peripherals 390 via wireless interface 330. During a surgery, echoes of ultrasound waves sent from the probe 10 into an area of interest are detected at the probe 10. Then, echo signals are communicated from the probe 10, via the wireless interface 310, to the processor 380. The processor 380 performs necessary signal processing and adaptation of the signals to create an image signal. The image signal corresponding to an image of the surgical region of interest is communicated over wireless interface 320 to the movable display 370. The display 370 is configured to be positioned in the sterile operating field adjacent to the surgical site and provides an image of the scanned region to guide the surgeon during the surgery. For example, the display 370 may be clamped onto a surgical drape near the surgical site or onto surgeon's gown.

Figure 4:
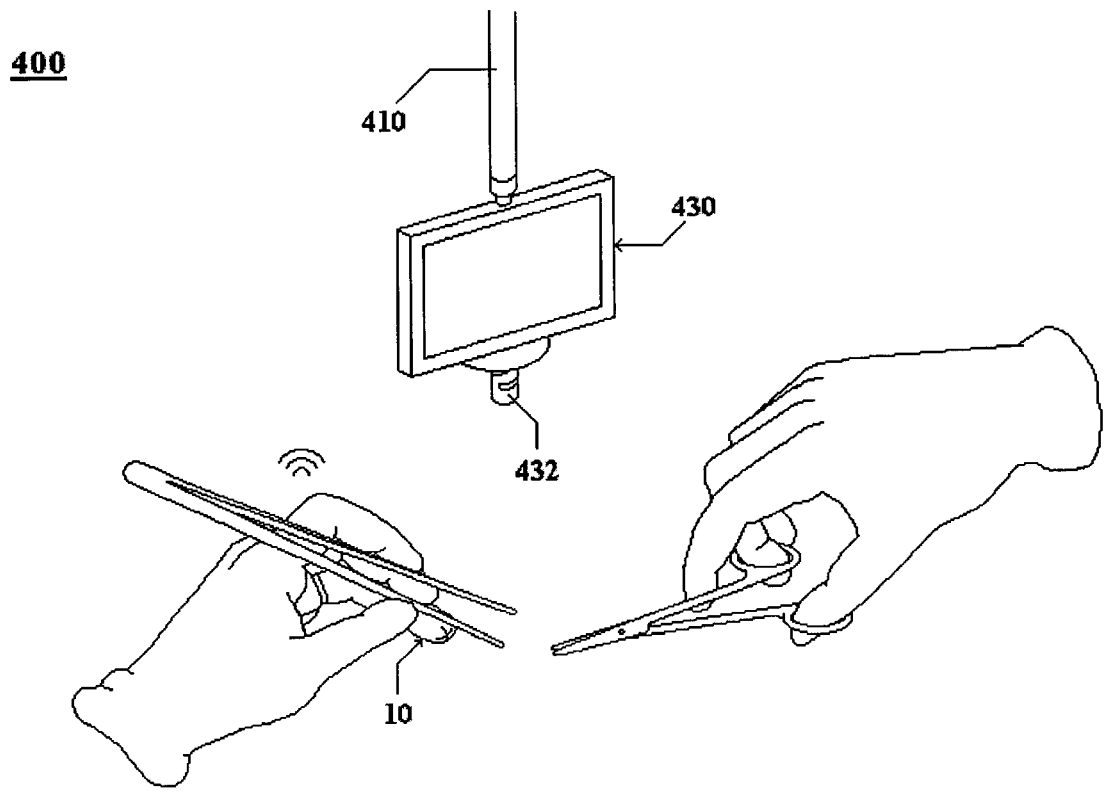
FIG. 4 is a general diagram that illustrates another embodiment of the ultrasound system.

Referring to FIG. 4, another embodiment of an ultrasound system 400 is disclosed. In this particular embodiment, a display 430 is connected to an articulated arm 410. The articulated arm 410 may be moved by a user, such as the surgeon or nurse, to a particular position that is conducive to proper surgical view. The user may manipulate the position of the display using a sterilizable attachable/detachable grasping surface such as a handle 432, which is preferably sterile during a surgery. The grasping surface may take other forms, such as a sterilizable transparent surface that is shaped to fit over all or part of the display during the surgery. The articulated arm 410 may be connected to the ceiling or other stationary object in the surgical room, and positioned by the surgeon over the operating table and conveniently close to the surgical field. Because the grasping surface is sterile, the surgeon or another member of the surgical team can reposition the display 430 as necessary without compromising the sterility of the surgical field. Any suitable structure can be used for the articulated arm 410, including an arm with one or more joints providing multiple degrees of freedom and an arm with flexible segments. If desired, the arm 410 may be controlled remotely, for example by servo motors controlled by a controller or a speech recognition system.

Figure 5:
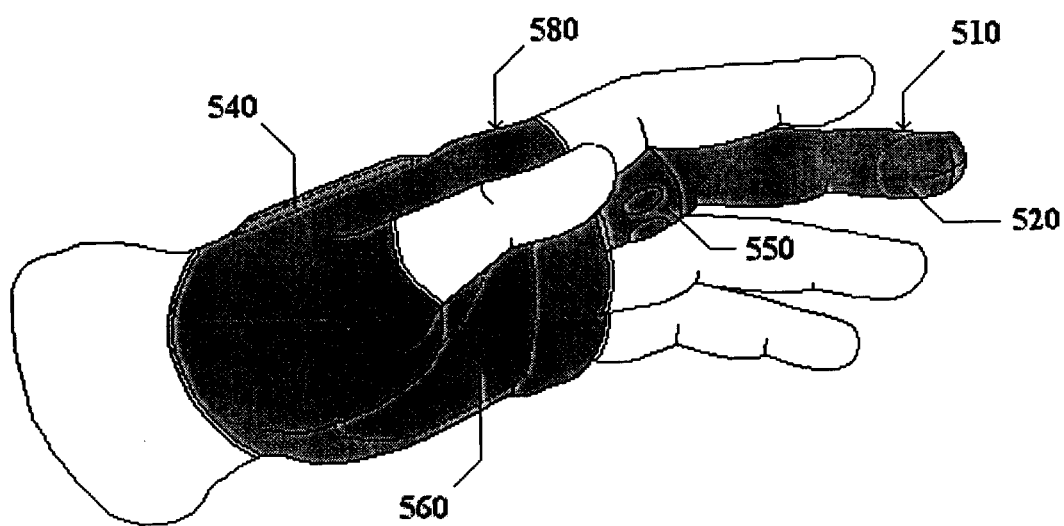
FIG. 5A is a general diagram that illustrates another embodiment where the probe, processor, display, and battery are worn on one hand.
FIG. 5B is a dorsal view of the embodiment of FIG. 5A.
FIG. 5C is a volar view of the embodiment of FIG. 5A.
Figure 5:
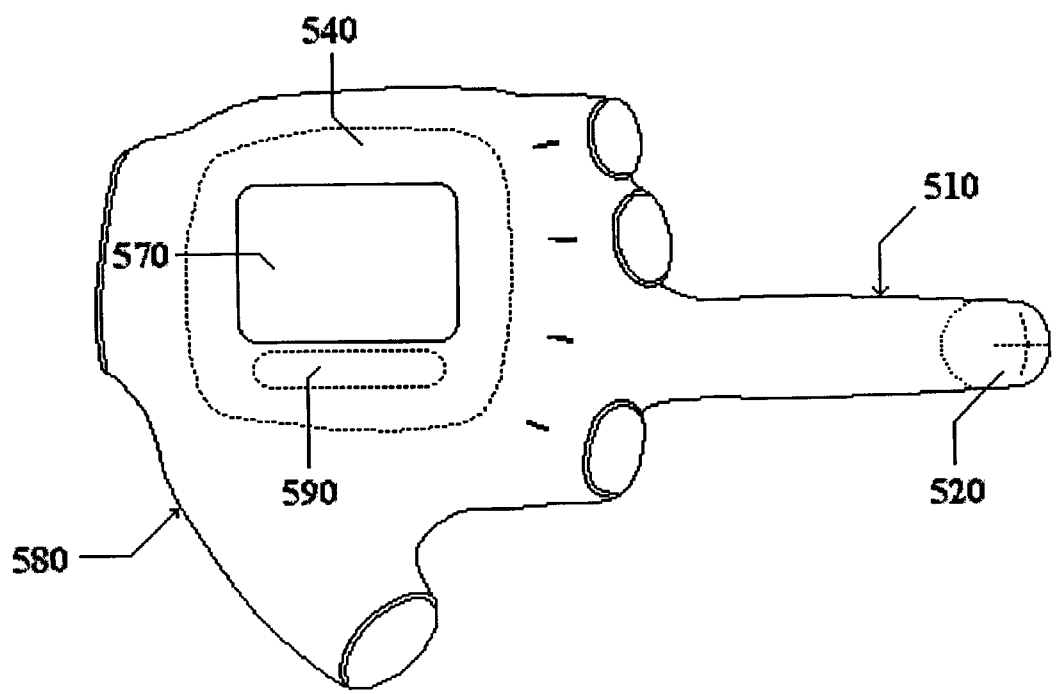
Figure 5:
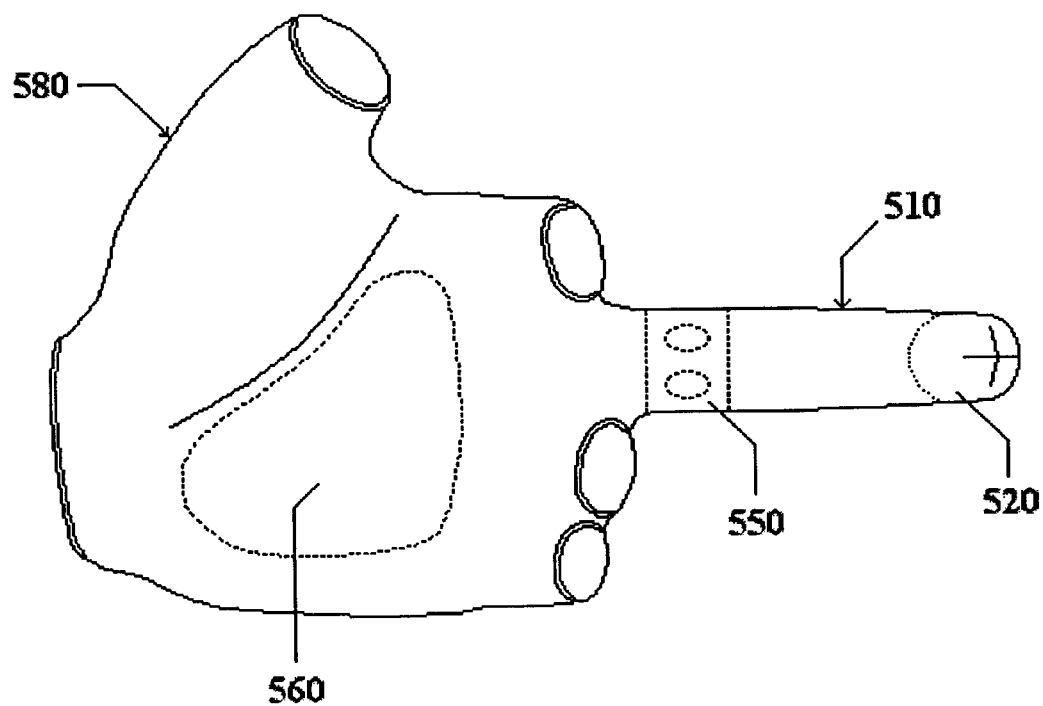
Figure 6:
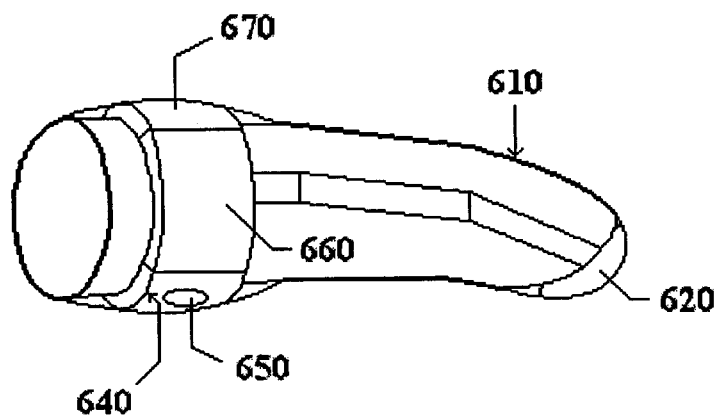
FIG. 6 is a general diagram that illustrates an embodiment of an ultrasound system where basic elements of the system fit on one finger of a user's hand.

In some embodiments the display is also wearable like the probe (such as in FIGS. 2, 5B, 6). The display may be worn together with or separate from the probe. In other embodiments, the display, such as displays 30 and 370, is appropriate to position in a sterile operating field (FIGS. 1, 3). For example, it may be releasably attached to a surgical cloth or a drape. In other embodiments, the display, such as display 430, is positioned close to a surgeon's sight through an articulated arm 410 which is preferably mounted on the ceiling (FIG. 4). When the display provides visual information to the surgeon, the display is preferably positioned near the surgical field such that the surgeon can easily shift his or her field of vision from the surgical site to the display with little or no head motion. This makes it convenient to use the information generated by the ultrasound system during the surgery to guide or otherwise assist the surgeon in making cutting or dissecting operations without interrupting the surgery. Any one or more of the wireless links in different embodiments illustrated in any of the figures may be replaced by cable connections in some other embodiments and vice versa.

Referring to FIG. 5A, another embodiment of an ultrasound system 500 is illustrated. In this embodiment, all of the elements of the ultrasound system, specifically the probe 510, the processor 540 and the display, are disposed on a hand of a user, such as a surgeon. The elements of the ultrasound system may be disposed within different layers and or covers of a structure, such as the hand receiving structure as shown in FIG. 5A. For example, the illustrated structure includes a cover 580 made of an elastic material. A battery unit 560 and a processor 540 are shown to be embedded within the structure for wearable use by the surgeon. The structure of FIG. 5A can be integrated into a surgical glove that isolates the entire hand of the surgeon from the surgical site.

FIGS. 5B and 5C are dorsal and volar views of the embodiment of FIG. 5A. This embodiment disposes all basic elements of an ultrasound system on a hand of a user. Referring to FIG. 5B, a display element 570 integrated with a processor 540 may be positioned on the dorsum of a hand to provide for visual viewing of ultrasound images. There may be a user interface 590 on the processor and/or a user interface 550 on the flexor surface of the finger at the tip of which an ultrasound transducer 520 is positioned.

Referring to FIG. 6, another embodiment of an ultrasound system 600 is illustrated. This compact ultrasound system 600 includes an ultrasound probe 610 that contains an ultrasound transducer 620 at its distal end. The illustrated self-contained ultrasound system 600 has a battery power supply 660 and also includes a display 670, and a processor 640 with a user interface 650 on the processor.

An example of the illustrated ultrasound system in its simplest form is a wearable intraoperative Doppler ultrasound system. It detects blood vessels and provides information about their presence and/or depth and/or size and/or type and/or flow properties. In a particular embodiment, the whole intraoperative Doppler ultrasound system fits on one finger (FIG. 6).

Signal processing for intraoperative Doppler function uses a difference filter which, at each depth of interest, filters out the stationary part of the signal (i.e., clutter) by using two or more samples acquired at a certain pulse repetition rate. In one embodiment, the output of the filter goes through an amplitude detector followed by an integrator. The output of the integrator is an indicator of the power of the flow signal as a function of depth. If the power is above a threshold, then the processor sends a signal indicating that a blood vessel is present. Preferably the user can adjust the threshold up or down, controlling the sensitivity of the system to small vessels with low spectral power. The depth at which the threshold is exceeded indicates the depth of the vessel. In one embodiment only the depth of the shallowest vessel is communicated to the user. In some alternative embodiments the processor also estimates and displays one or more of the following parameters: flow direction, flow speed, peak flow speed, and peak flow velocity, flow type (arterial or venous), etc. To estimate these parameters there are various well known techniques in the art of signal processing.

Figure 7:
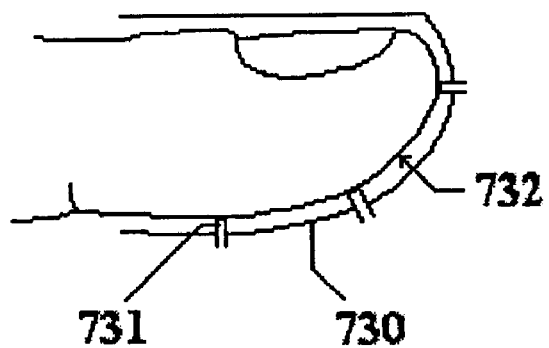
FIG. 7 schematically shows a tactile display on a user's fingertip.
Figure 8:
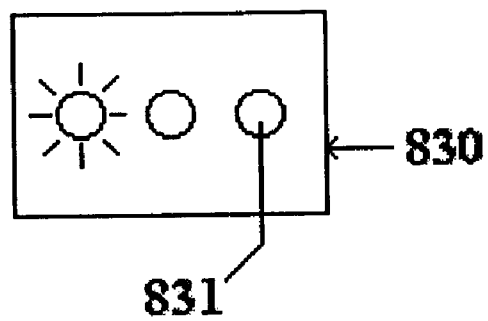
FIG. 8 is an illustration of a visual display that includes LEDs.

FIGS. 7 and 8 illustrate a tactile display and a LED display, respectively. The tactile display 730 may have at least one mechanically movable skin-contacting element such as a prong 731 that can touch the skin of the user 732 when activated. If there are plural prongs, each prong is disposed at enough distance to one another so that the user can distinguish two from one when both touch. The prongs present tactile display information such as the presence or absence of a certain caliber vessel in a selected range of depths below the tissue surface, for example. Again as an example, if there is more than one prong, each one may be assigned to presenting information gathered from different ranges of depth that may overlap to a determined extent, or to presenting different kind of information such as vessel type, or flow properties. The number of the prongs determines the amount and/or accuracy of the information that is presented. LEDs can be used in the same way. In FIG. 8 three LEDs 831 (one that is activated) are schematically illustrated on a visual display 830. There is at least one LED on a LED display. The color of the LED light can also be used to present various information to a user. For example, the same LED may emit green light when a vessel is detected by the system within distal one third, orange light if the vessel is within the middle one third, red light if the vessel is within the proximal one third of an investigated depth.

Figure 9:
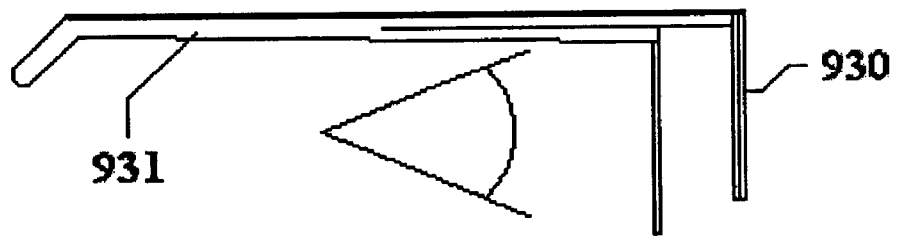
FIG. 9 is a schematic illustration of a display attached to eyewear to be used as a part of a surgical ultrasound system.
Figure 10:
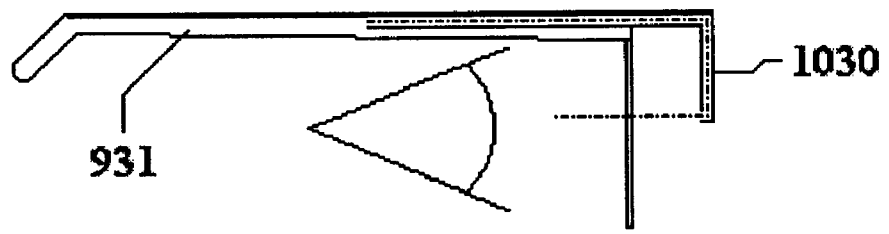
FIG. 10 is a schematic illustration of an image projecting system attached to eyewear to be used as a part of a surgical ultrasound system.

Referring to FIGS. 9 and 10 a visual display 930 and a projection system 1030 appropriate to present visual information obtained through an ultrasound system are illustrated respectively. The display 930 and the projecting system 1030 are shown to be attached to eyewear 931. While a display in front of an eye necessarily occludes a part of the eye's field of vision despite its small size, the systems that project an image onto a user's retina do not interfere with the user's field of vision using see-through reflective surfaces, so that the user can see both the ambient imagery (e.g., the surgical site) and the projected visual display information simultaneously.

Figure 11:
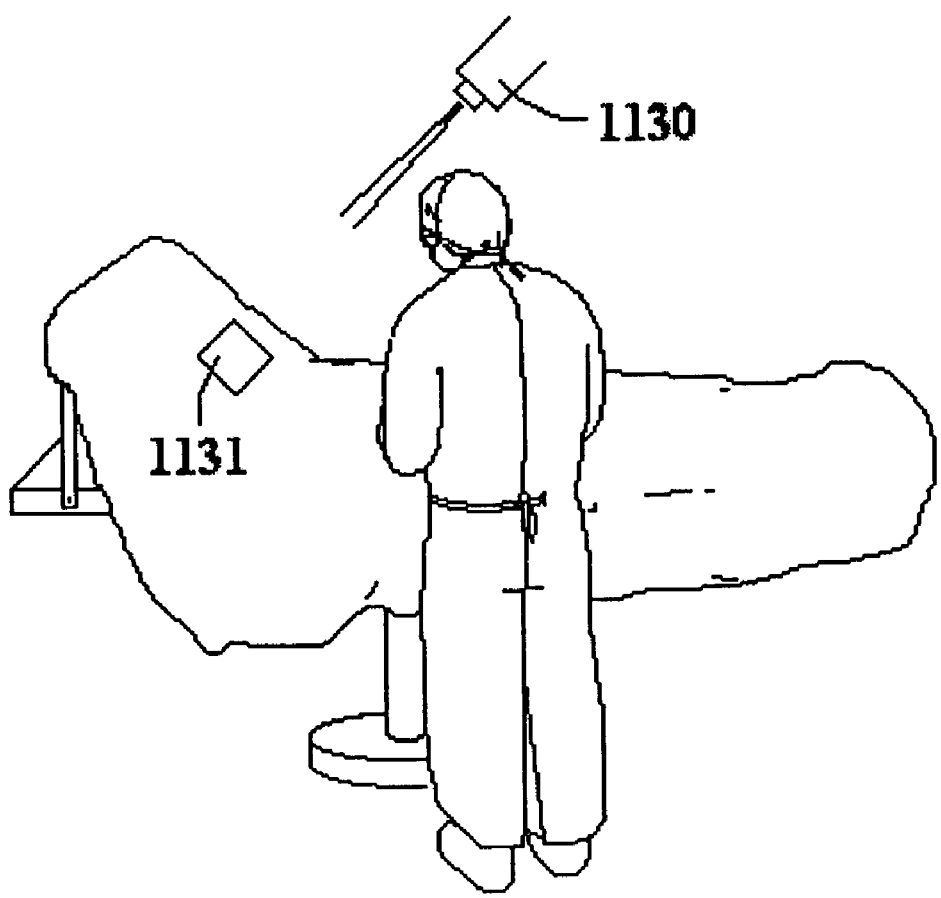
FIG. 11 depicts use of an ultrasound system where an image is projected on a surface in sterile operating field.

FIG. 11 depicts a scene from an operating room where the visual information generated by an ultrasound system is projected onto a surface 1131 in the sterile operating field by a projector 1130. Proximity of the surface to the surgical site allows the surgeon to operate while receiving the visual information with little or no head movements. The surface 1131 may be attached to a surgical drape near an incision, or the surface 1131 may be a surface of a surgical drape.

Figure 12:
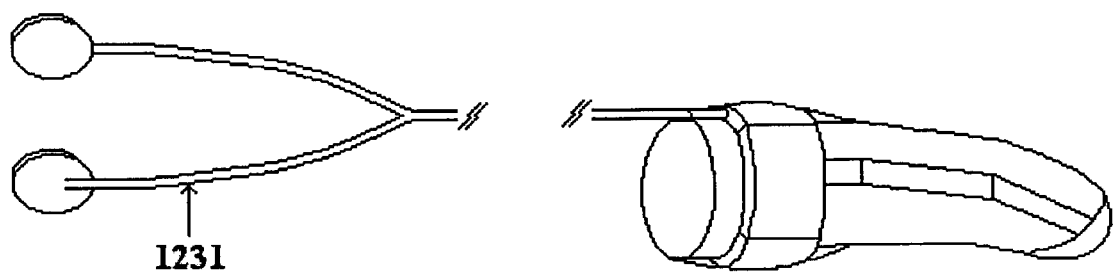
FIG. 12A is a general diagram that illustrates a version of the embodiment of FIG. 6 with earphones.
FIG. 12B is a general diagram that illustrates another version of the embodiment of FIG. 6 with speakers.
Figure 12:
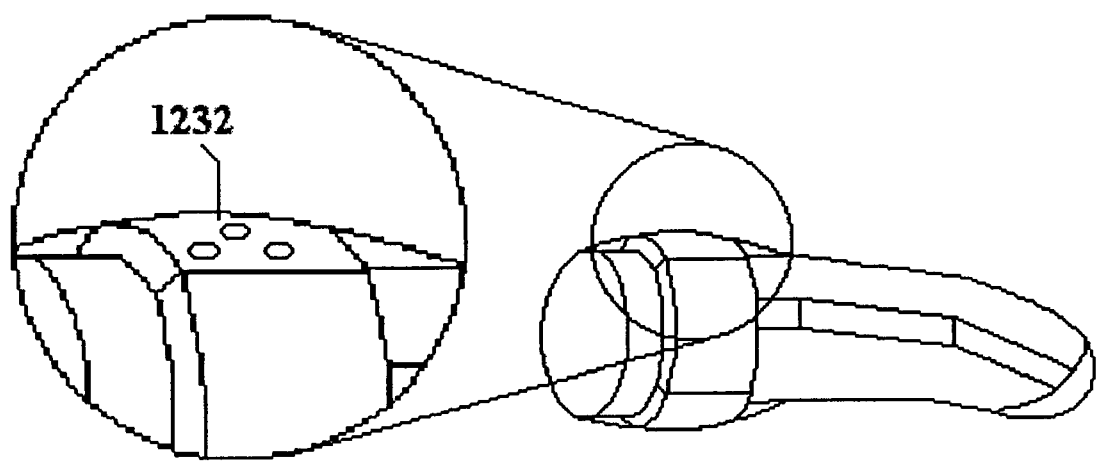

FIGS. 12A and 12B illustrates the ultrasound system of FIG. 6 where the audio output of the system is through an earphone 1231 or a speaker 1232.

In any embodiment where at least one of the ultrasound system elements is worn on the hand, that part of the system may be incorporated into a surgical glove so that it may also function as a surgical glove.

All elements of the ultrasound system that are intended to function in a sterile area are preferably substantially waterproof and can be sterilized and/or can be enclosed in an enclosure made of a substantially waterproof and sterilizable material at least during the surgery. At least the part of the enclosure that covers the display is preferably substantially transparent. Any part of the ultrasound system may also be disposable or reusable.

Another benefit provided is that the disclosed ultrasound system is ready to use by the surgeon at any time and at all locations during the surgery. The disclosed ultrasound system does not interfere with the flow of surgery or get in the way of the surgeon while using the system during surgery. For example, the system does not interfere with the surgeon's field of vision, general movements of the surgeon, or the movements of the surgeon's hands and fingers. Further, the disclosed ultrasound system displays information obtained and processed through the system in a visual, audio or tactile from that is conveniently accessed by the surgeon while performing surgery.

As used herein, the term "surgical site" refers to the tissues of a surgical patient adjacent to an actual or intended surgical action during or immediately prior to a surgery. The region around a surgical site is generally sterile, and this region with all sterile objects that are allowed to enter into this region during the surgery is referred to here as the "sterile operating field".

The above disclosed subject matter is to be considered illustrative, and not restrictive, and the appended claims are intended to cover all such modifications, enhancements, and other embodiments which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A surgical ultrasound system comprising:
   an ultrasonic probe wearable on a portion of a user's body within a sterile operating field and operative to insonify a surgical site and to receive echoes from the surgical site; and
   a display coupled via a processor with the wearable ultrasonic probe, wherein the display is selected from the group consisting of: a display positioned within a sterile operating field during a surgery; a display carried by an articulated arm and positioned near a sterile operating field during a surgery, said articulated arm configured to be repositioned under the direction of a user without compromising sterility of the sterile operating field; and a wearable display.

2. The surgical ultrasound system of claim 1, wherein the display comprises a wearable display.

3. The surgical ultrasound system of claim 2, wherein the wearable display is configured to worn on a human body part selected from the group consisting of: a hand, a wrist, a forearm, and a head.

4. The surgical ultrasound system of claim 2, wherein the wearable display comprises eyewear.

5. The surgical ultrasound system of claim 2, wherein the wearable display comprises a wearable image projection device operative to project an image onto a surface.

6. The surgical ultrasound system of claim 5 wherein the surface comprises a retina surface.

7. The surgical ultrasound system of claim 2, wherein the wearable ultrasonic probe and the wearable display are both disposed on a structure configured and shaped to receive at least a part of a hand of a user.

8. The surgical ultrasound system of claim 2, wherein the processor comprises a wearable processor.

9. The surgical ultrasound system of claim 8, wherein the wearable ultrasonic probe, the wearable processor, and the wearable display are all disposed on a structure configured and shaped to receive at least a part of a band of a user.

10. The surgical ultrasound system of claim 1, wherein the display comprises a surface operative to present visual information, said surface positioned within the sterile operating field near a surgical site during a surgery.

11. The surgical ultrasound system of claim 10, wherein the surface is selected from the group consisting of: a screen and a surgical drape.

12. The surgical ultrasound system of claim 1, wherein the display comprises a visual display.

13. The surgical ultrasound system of claim 12, wherein the visual display comprises a wearable flat panel display comprising a flexible screen.

14. The surgical ultrasound system of claim 12, wherein the visual display comprises at least one Light Emitting Diode.

15. The surgical ultrasound system of claim 1, wherein the display comprises an audio display.

16. The surgical ultrasound system of claim 15, wherein the audio display is selected from the group consisting of: an earphone and an audio speaker.

17. The surgical ultrasound system of claim 1, wherein the display comprises a tactile display.

18. The surgical ultrasound system of claim 17, wherein the tactile display comprises at least one movable skin-contacting element.

19. The surgical ultrasound system of claim 1, wherein the wearable ultrasonic probe comprises at least one ultrasound transducer.

20. The surgical ultrasound system of claim 19, wherein the ultrasound transducer operates as an ultrasound transmitter and receiver.

21. The surgical ultrasound system of claim 19, wherein the ultrasound transducer is selected from the group consisting of a piezoelectric ceramic transducer, a piezoelectric polymer transducer, a piezoelectric ceramic/polymer composite transducer, and a micromachined transducer.

22. The surgical ultrasound system of claim 19, wherein the ultrasound transducer is selected from the group consisting of: a single element transducer, a multiple element transducer, a 1D array transducer, a 1.25D array transducer, a 1.5D array transducer, a 1.75D array transducer, and a 2D array transducer.

23. The surgical ultrasound system of claim 1, further comprising a wireless transceiver coupled with the processor.

24. The surgical ultrasound system of claim 1, wherein the processor comprises a wearable processor.

25. The surgical ultrasound system of claim 1, wherein the wearable ultrasonic probe is carried by a sleeve shaped to fit over a finger of a user.

26. The surgical ultrasound system of claim 25, wherein the sleeve comprises a flexible region positioned to align with a joint of the finger of the user.

27. The surgical ultrasound system of claim 1, further comprising a battery, the wearable ultrasonic probe coupled with the battery.

28. The surgical ultrasound system of claim 1, further comprising a user interface, the user interface coupled with the processor.

29. The surgical ultrasound system of claim 1, wherein the wearable ultrasonic probe is covered with an elastomeric material.

30. The surgical ultrasound system of claim 29, wherein the elastomeric material comprises an acoustically transparent region, the acoustically transparent region disposed adjacent a transducer element of the wearable ultrasonic probe.

31. The surgical ultrasound system of claim 1, wherein the display is carried by the articulated support arm.

32. The surgical ultrasound system of claim 31, wherein at least one of the articulated support arm and the display carried by the articulated support arm carries a sterile grasping surface during the surgery.

33. The surgical ultrasound system of claim 32, wherein the sterile grasping surface comprises a handle.

34. The surgical ultrasound system of claim 31, wherein the articulated support arm and therefore the display carried by the articulated support arm are positioned by remote control.

35. The surgical ultrasound system of claim 31, wherein the articulated support arm is mounted near an operating table and is configured to support the display in a range of user-selected positions above the operating table.

36. A method of using an ultrasound system during a surgery, the method comprising:
    (a) placing a wearable ultrasound probe comprising an ultrasound transducer element of the ultrasound system onto a hand of a surgeon;
    (b) acquiring echoes from a surgical site with the wearable ultrasound probe;
    (c) generating display information from the echo signals; and
    (d) providing the display information to the surgeon during the surgery while the surgeon's head is positioned to view the surgical site via a display selected from the group consisting of: a display positioned within a sterile operating field during the surgery; a display carried by an articulated arm and positioned near a sterile operating field during the surgery, said articulated arm configured to be repositioned under the direction of the surgeon without compromising sterility of the sterile operating field; and a wearable display.

37. The method of claim 36, wherein (d) comprises providing the display information to the surgeon as visual information.

38. The method of claim 36, wherein (d) comprises providing the display information to the surgeon visually on a surface positioned such that the surgeon can view the display and the surgical site without substantial head movement.

39. The method of claim 36, wherein (d) comprises projecting the display information onto a retina of the surgeon.

40. The method of claim 36, wherein (d) comprises providing the display information to the surgeon as audio information.

41. The method of claim 36, wherein (d) comprises providing the display information to the surgeon as tactile information.

42. The method of claim 36, further comprising performing a surgical action in response to the display information communicated to the surgeon during the surgery.

43. The method of claim 42, wherein the surgical action is one of piercing, cutting and dissecting.

44. The method of claim 36, further comprising using a wearable user interface of the ultrasound system after placing the wearable ultrasound probe onto the hand of the user.

45. The method of claim 44, further comprising adjusting a system parameter of the ultrasound system via the user interface.

46. The method of claim 45, wherein the system parameter comprises a sensitivity level of the ultrasound system.

47. The method of claim 36, wherein the display information comprises Doppler ultrasound information.

48. The method of claim 36, wherein the wearable probe is mounted on the hand of the surgeon.

49. The method of claim 36, wherein the wearable probe is operative to hold itself in place on the hand of the surgeon during use.

50. A method of using an ultrasound system during a surgery, the method comprising:
 (a) placing a wearable ultrasound probe comprising an ultrasound transducer element of the ultrasound system onto a hand of a surgeon;
 (b) acquiring echoes from a surgical site with the wearable ultrasound probe while the hand of the surgeon is still able to contribute to the performance of the surgery;
 (c) generating display information from the echo signals; and
 (d) providing the display information to the surgeon during the surgery while the surgeon's head is positioned to view the surgical site via a display selected from the group consisting of: a display positioned within a sterile operating field during the surgery; a display carried by an articulated arm and positioned near a sterile operating field during the surgery, said articulated arm configured to be repositioned under the direction of the surgeon without compromising sterility of the sterile operating field; and a wearable display.

* * * * *